United States Patent [19]

Baker

[11] Patent Number: 5,106,582
[45] Date of Patent: Apr. 21, 1992

[54] SPECIMEN TEST SLIDE AND METHOD OF TESTING FOR FECAL OCCULT BLOOD

[75] Inventor: Josefina T. Baker, Cupertino, Calif.

[73] Assignee: Smithkline Diagnostics, Inc., San Jose, Calif.

[21] Appl. No.: 630,453

[22] Filed: Dec. 18, 1990

[51] Int. Cl.⁵ .............................................. G01N 33/72
[52] U.S. Cl. ...................................... 422/58; 422/56; 422/61; 436/66
[58] Field of Search ................................... 422/56–58, 422/61; 436/66, 169

[56] References Cited

U.S. PATENT DOCUMENTS

| | | | |
|---|---|---|---|
| 3,996,006 | 12/1976 | Pagano | 422/58 X |
| 4,042,329 | 8/1977 | Hochstrasser | 436/66 X |
| 4,199,550 | 4/1980 | Wielinger et al. | |
| 4,225,557 | 9/1980 | Hartl et al. | 422/58 X |
| 4,365,970 | 12/1982 | Lawrence et al. | 422/58 X |
| 4,486,536 | 12/1984 | Baker et al. | 422/58 X |
| 4,645,743 | 2/1987 | Baker et al. | 422/58 X |
| 4,742,002 | 5/1988 | Guadagno | 436/66 X |
| 4,772,560 | 9/1988 | Attar | 422/58 X |
| 4,808,379 | 2/1989 | Wardlaw | 436/66 X |

FOREIGN PATENT DOCUMENTS 0117689 9/1984 European Pat. Off. .

Primary Examiner—Robert J. Hill, Jr.
Attorney, Agent, or Firm—William H. May; Arnold Grant; Richard P. Burgoon, Jr.

[57] ABSTRACT

A specimen slide in accordance with the present invention comprises a front panel including a test material placement side and a portion of a test sheet, the test material placement side including at least one aperture which is configured to accept a test sample through the aperture onto the test sheet, and a back panel including a developing side through which the opposite side of the test sheet is exposed. An indicating means is located on the developing side portion of the test sheet within proximity to, but not directly on, the portion of the test sheet directly opposite to the aperture.

24 Claims, 1 Drawing Sheet

SPECIMEN TEST SLIDE AND METHOD OF TESTING FOR FECAL OCCULT BLOOD

FIELD OF THE INVENTION

The present invention relates to devices and methods for testing specimens and more particularly to an improved specimen test slide for fecal occult blood.

BACKGROUND OF THE INVENTION

Fecal occult blood testing has become a popular, widely used procedure useful in the detection of relatively small amounts of blood in fecal specimens. This wide use and popularity arises primarily because fecal occult blood testing is non-invasive, simple and inexpensive to perform. Because the presence of fecal occult blood in a specimen is a symptom that may be associated with colon cancer or a precursor to colon cancer, fecal occult blood testing is often routinely used as a screening tool. The routine screening of patients by means of fecal occult blood testing has helped to detect colon cancer at a stage where the disease is readily treatable.

A popular form of fecal occult blood testing utilizes a guaiac treated test sheet where a fecal material specimen is smeared on a front, or, "test material placement" side of the test sheet. The fecal material has a tendency to diffuse through the test sheet, defining a region on a side of the sheet opposite to the test material placement side. The portion of the sheet opposite to where the test material is smeared is the back, or, "developing" side of the sheet, and the area on the developing side of the test sheet where the fecal material diffuses through from the test material placement side of the test sheet is referred to herein as the "diffused region" or the "diffused area". A developing solution is applied to the developing side of the sheet directly onto the diffused region, and if a color change is indicated, blood may be present in the fecal specimen.

There has been an on-going need to obtain, transport and process the specimens of the fecal occult blood test in a manner that is as convenient and as aesthetically acceptable as possible. One form of specimen collection device that has gained wide popularity is a slide formed from folded paper or cardboard. The slide includes guaiac treated paper to which the fecal specimen is applied through a "test window" or "aperture" located on the test material placement side of the test sheet, and a cover which is closed once the specimen application is completed. A flap in the back of the slide may be opened to reveal the developing side of the guaiac treated paper for subsequent application of developer onto an area of the developing side of the test sheet directly opposite to the aperture or apertures, i.e., directly onto the diffused region. A positive result, that is, one indicating the presence of blood in the fecal sample, is determined by the presence of (usually) a blue color, and the intensity thereof provides further information as to the amount of blood present in the fecal sample.

Specimen slides for fecal occult blood tests generally have test windows of varying sizes. In an attempt to standardize the sample amount applied through the test windows and in an effort to mitigate against over- or under- application of sample, instructions for sample application are ordinarily provided to the patient. These instructions vary, but are generally intended to provide direction to the patient in an effort to limit the amount of sample smeared into the test window, i.e., "apply a thin smear"; "a pea size"; or "the size of a match head".

The quantity of the sample on the slides returned to the laboratory varies from trace amounts, which are insufficient for proper testing, to very excessive amounts, which also create technical, as well as aesthetic, problems. It is often the case that when there is too much sample on the test material placement side, the developing side of the slide is fully covered with the colored stain of the diffused sample. This makes reading of test results based on color intensity difficult and usually impossible.

Errors on the part of the technician developing the test slide may also occur. For example, if the technician inadvertently adds developer to the test material placement side of the test slide, as opposed to the developing side, the sample can be flooded with the developing solution, leading to incomprehensible, incorrect or misleading results, due to reconstitution of the sample. Furthermore, the instructions for application of the developing solutions require application thereof directly onto the diffused region. It is often the case, particularly when an insufficient amount of sample is present, that far too much developing solution will be added directly onto this area in an attempt to compensate for the lack of sufficient sample. This also has the effect of flooding the diffused region, which can result in incomprehensible, incorrect or misleading results, i.e. the intensity of the color can be artificially altered.

Most of the problems associated with differing amounts of sample added to the test slide by the patient are predicted upon the inexperience of the patient with such test slides. Given the very nature of, for example, fecal sample materials, different individuals will react differently to applying such a sample to a test slide. Therefore, while instructions can be provided to the patient as to how much of a sample should be placed in the test window area, consistent amounts of sample across of wide-ranging group of patients are not obtainable, as experience has demonstrated. Additionally, the technician who attempts to develop a test on a test slide that includes either inadequate or excessive amounts of sample could possibly provide incorrect results to the patient or the patient's physician; thus the medical technician who attempts, albeit incorrectly, to compensate for incorrect sample amounts could possibly provide the patient or the patient's physician with results that do not lead to additional (and necessary) tests, or with results that lead to additional (but unnecessary) tests. Thus, the technician who provides such erroneous results could be exposed to legal liability.

Because the performance of the test is dependent on the reproducibility, ease of use by patients, as well as efficient, yet simple, sampling/developing procedures, an improved specimen test slide taking the above factors into account is not only desirable, but necessary.

SUMMARY OF THE INVENTION

The present invention overcomes the limitations and drawbacks noted above.

A most preferred embodiment of a specimen slide in accordance with the present invention comprises a front panel including a test material placement side and a portion of a test sheet, the test material placement side including at least one aperture which is configured to accept a test sample through the aperture onto the test sheet, and a back panel including a developing side through which the opposite side of the test sheet is exposed. An indicating means is located on the developing side portion of the test sheet within proximity to, but not directly on, the portion of the test sheet directly opposite to the aperture. The location of the indicating means relative to the aperture is critical and essential to the performance of the specimen slide. The indicating means is most preferably a target printed directly onto the test sheet.

The size and shape of the aperture is configured such that the aperture is completely filled with the test sample. The width of the aperture is preferably less than the height of the aperture. Two apertures are most preferably included in the front panel, and the juxtaposition of the apertures is such that the inner edges thereof are substantially non-parallel with each other. Most preferably, the apertures have a "letter C" configuration such that the interior portion of each "letter C" aperture faces the indicating means.

The location of the indicating means relative to the aperture is such that when a developing solution is added onto the indicating means, the solution migrates completely through the portion of the test sheet directly opposite to the aperture.

To use the specimen slide, the patient completely fills the aperture with, e.g., a fecal specimen. A developing solution is then added onto the indicating means. The solution, having a tendency to migrate across the test sheet, migrates through an area of the test sheet directly opposite to the aperture, including the diffused region. By specifically locating the indicating means at a defined location relative to the aperture, the developed solution migrates away from this stained region, which surprisingly and unexpectedly enhances the color intensity of the developed solution, and hence the readability of the color intensity, as compared to previous specimen test slides.

DETAILED DESCRIPTION OF PREFERRED EMBODIMENT

Figure 1:
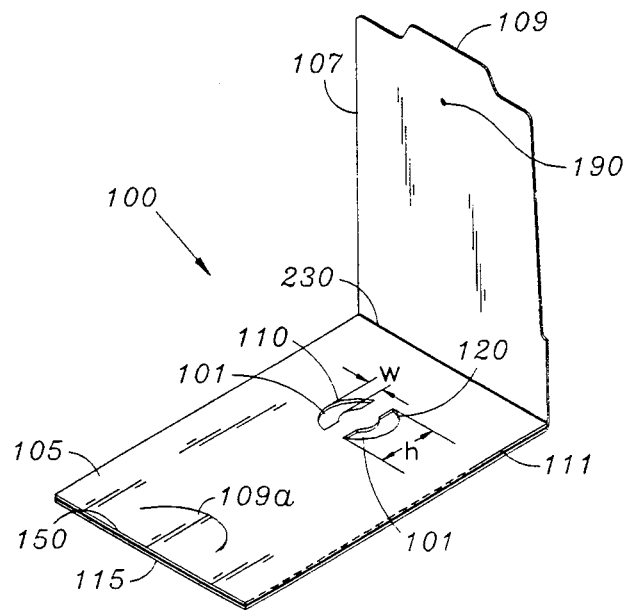
FIG. 1 is a perspective view of the front side of a preferred embodiment specimen test slide in accordance with the present invention where the test windows have a letter C configuration and each test window faces the other.
Figure 2:
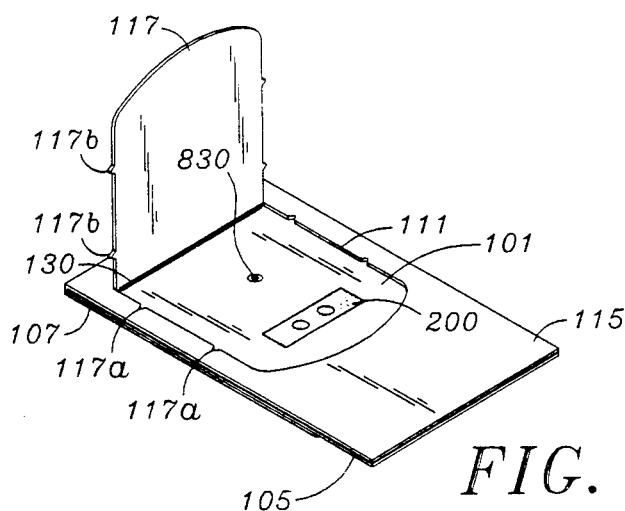
FIG. 2 is a perspective view of the back panel of the device shown in FIG. 1

With reference to FIG. 1 and 2, a most preferred embodiment of a device in accordance with the present invention is in the form of a specimen slide 100 and includes a front panel 105, with a corresponding front panel cover flap 107 (shown in an open position in FIG. 1) and a back panel 115, with a corresponding back panel cover flap 117. Panel 105 includes in the central region thereof a test material (sample) placement area which preferably includes two apertures 110, 120 and test sheet 101 of absorbent material fixed between the front panel 105 and back panel 115.

Cover flap 117 (shown in its open position in FIG. 2) is defined in the back panel 115 by an outline of perforations 111 and a crease 130 which serves as a hinge. The perforations 111 are spaced to define a plurality of bridges, each bridge comprising bridge portions 117a and 117b. The bridges hold flap 117 in place until the bridges are broken as flap 117 is opened along the perforations 111 to reveal the backside of test sheet 101. In the embodiment disclosed herein, sheet 101 is filter paper which carries a reagent which will react with hemoglobin components from blood and a peroxide solution to form a visible colored compound. In the embodiment disclosed herein, test sheet 101 is Whatman Grade #1 filter paper (Whatman Paper Ltd., Springfield Mill, Kent, United Kingdom). The reagent may be, for example, guaiac, tetramethyl benzidine, ortho tolidine, and other similar chromogens. In the embodiment disclosed herein, the reagent carried by the sheet 101 is guaiac. An area defining monitors suitable for indicating the performance of the guaiac carrying test sheet 101 and reagents which may be applied thereto is indicated at 200 and may be of the form described, for example, in U.S. Pat. No. 4,365,970.

The specimen slide 100 is preferably formed from a single sheet or panel of paper or cardboard. The cardboard is die-cut to form apertures 110 and 120 (best viewed in FIG. 1 and shown in phantom in FIG. 3), as well as the perforations to define flaps 107 and 117. A tab 109 is also formed at the other edge of flap 107. Tab 109 is adapted to engage a semi-circular slit 109a formed near an outer edge 150 of the frontal panel 105. The slit 109a is also formed by, for example, die-cutting during the manufacturing process of the slide 100.

Specimen sheet 101 is positioned and fixed by a suitable adhesive or glue. The front and back panels 105 and 115 are folded along the edge 150 and are pressed and held together by means of a suitable glue or adhesive. A drop of glue 190 holds the front panel 105 and front panel cover flap 107 together until slide 100 is ready for use.

In order to effectuate the placement of developing solution onto test sheet 101, means are provided for indicating the placement of the developing solution onto test sheet 101 onto an area of the test sheet opposite to apertures 110 and 120. For example, a target area, preferably in the form of a target 830 (FIG. 2 and FIG. 3), can be printed directly onto test sheet 101. Target 830 is the most preferred means for directing the medical technician to apply the developing solution onto the test sheet 101. Alternative means for indicating can include, for example, any printed locator for directing the placement of the developing solution onto test sheet 101.

The location of the indicating means is critical. By ensuring that the indicating means is properly located relative to the aperture(s), then irrespective of the size, shape or specific juxtaposition of the aperture(s), or the specific type of filter paper utilized, the advantages derived herein can be realized. In effect, the location of the aperture relative to the indicating means is determined by the objective of ensuring that the developing solution can contact the test sample, react therewith to form a reaction product (if any), and carry any reaction product away from the stained region onto a relatively clean area of test sheet 101 adjacent to such a stained region. For these reasons, the location of the indicating means is advantageously located relative to the location of the aperture, as will be described in detail below.

Figure 3:
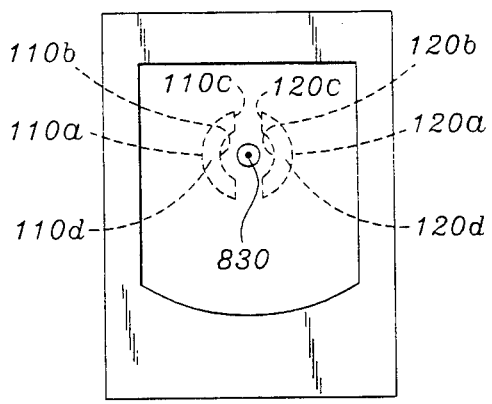
FIG. 3 is a plan view of the back panel of the device shown in FIG. 1 where the test windows are designated as phantom lines.

With reference to FIG. 3, and with respect to the embodiment disclosed herein, target 830 is advantageously located between about 1.5 and about 2.5 times, and preferably about 2.0 times the width of an aperture from outer edges 110a and 120a of apertures 110 and 120, respectively. As used herein, the term "outer edge" is defined as the edge of an aperture located furthest from the target area as defined, including target 830, "inner edge" is defined as the edge of the aperture opposite to the outer edge, and "times" is an alternative term to the mathematical expression referred to as "multiplication" or "multiplied".

As an alternative method for locating the indicating means relative to the aperture, the distance between the outer edge of one aperture and the outer edge of at least one other aperture is advantageously between about 3.0 and about 5.0 times, and preferably about 4.0 times the width of an aperture such, that the indicating means is located at the midpoint between the apertures. As a further alternative, the indicating means is advantageously located between about 2.0 and about 4.0 times and preferably about 3.0 times one half of the width of the aperture from the approximate center of the aperture. As used herein, the "approximate center" of each aperture is defined as a point approximating call-out designations 110d and 120d (FIG. 3). i.e. a point located interior to an aperture at a point approximating about one-half of the height and about one-half of the width.

Preferably, the width of the aperture is less than the height of the aperture. "Height" is defined as the measured distance "h" in FIG. 1 and width is defined as the measured distance "w" in FIG. 1. The height of the aperture is advantageously about 5 times to about 1.5 times than the width of the aperture. Most preferably, the height is about 4 times the width of the aperture. The width is advantageously about 0.25 cm to about 1.00 cm and most preferably about 0.50 cm in length.

When two apertures are utilized, it is essential that the inner edges of the apertures be substantially non-parallel with each other. As used herein, the term "parallel" is accorded its usual definition, e.g. everywhere equidistant. "Substantially non-parallel" as used herein is indicative of the relative relationship between the inner edges of the aperture. Thus, the inner edges of the two apertures are substantially non-parallel if the distances between the inner edges are substantially non-equidistant. When more than two apertures are utilized, it is essential that the inner edges of the apertures be substantially non-partallel with each other as previously disclosed. When a single aperture having a straight line inner edge is utilized, it is essential that the distance between the top inner edge corner of the aperture and the indicating means be substantially greater or substantially less than the distance between the inner edge corner opposite to the top inner edge corner and the indicating means. Under this scheme, the indicating means can be described as the apex of a triangle, whereby the triangle is formed by: a line from the indicating means to the top inner edge corner; the inner edge; and a line from the inner edge corner opposite to the top inner edge corner and the indicating means. In this scenario, the triangle thus formed is not an equilateral triangle, given the length differentials described above.

Most preferably, the inner edge of each aperture(s) is curvilinear in nature such that a portion of the inner edge, or the entire inner edge, is bounded by a curved line. If only a portion of the inner edge of an aperture is curvilinear, the remaining portion thereof can be parallel with the inner edge of another aperture. In such a situation, at least one-half of the inner edge is preferably curvilinear. The curved line is advantageously positioned interiorly to the aperture(s). By way of example and not limitation and referencing FIG. 3, inner edge portion 110c and inner edge portion 120c are parallel to each other; however, inner edge portion 110b and inner edge portion 120b are curvilinear such that the inner edges of aperture 110 and 120 are substantially non-parallel to each other.

The outer edge of each aperture can also be curvilinear in nature. Most preferably, the entire outer edge is curvilinear. Accordingly, in the most preferred embodiment, the apertures each have a "letter C" configuration. As used herein, the term "letter C" configuration is meant to describe the configurational shape of an aperture as depicted in FIG. 1 and FIG. 3. Most preferably, the apertures each face one another.

For the embodiment disclosed herein, the most preferred measurements for the apertures would be such that the height of each aperture is about 2.0 cm, the width of each aperture is about 0.5 cm, and the distance between the outer edges of the apertures is about 2.0 cm, such that the distance between the outer edge of each aperture and target 830 is about 1.0 cm and the distance between the approximate midpoint of each aperture and target 830 is about 0.75 cm.

In using the specimen slide 100, fecal specimens are placed onto test sheet 101 through apertures 110 and 120 such that the specimens completely fill apertures 110 and 120. The patient closes the specimen slide 100 by folding front panel cover flap 107 along crease 230 and inserting tab 109 beneath slit 109a. The specimen slide 100 is transported to the physician's office or laboratory for analysis. With reference to FIG. 2, the analysis of the fecal specimens carried by specimen slide 100 may be accomplished in an advantageous manner, i.e. without reopening the specimen slide 100 at front panel cover flap 107 to gain access to apertures 110 and 120. Back panel cover flap 117 is opened by separating bridge portions 117a from 117b. A developing solution is applied to the back of the test sheet 101 onto target 830 to form a screening test for occult blood in the specimen.

Developing solution is most usually applied via a drop-wise application to the developing side of filter paper 101. As such, as these drops come in contact with test sheet 101 and are absorbed therein, there is a tendency for the solution to migrate outwardly from the point of contact, usually in a radial direction. Two to three drops of developing solution are added to the test sheet 101 by addition thereto onto target 830. After testing, the entire slide 100 may be properly disposed of.

Sheet 101 may be sensitized for other analytes and the device may be adapted for collecting other types of specimens, such as mucosic, viscous materials. Several slides may be attached side-by-side, each having a different reagent on sheet 101, such that testing of several analytes can be effectuated.

Different filter papers can be utilized for test sheet 101 such that adjustment of the location of the outer edges of the aperture(s) relative to the location of the target area or to one another is possible. Preferably, the composition of the filter paper is cotton fiber, although wood/cotton fiber or glass/cotton fiber combinations can be utilized. Three factors are of importance in determining the location of the outer edges of the apertures relative to the target area, these being the thickness, particle size relation and flow rate of the filter paper.

The thickness of the filter paper is preferably between about 0.10 mm and about 0.26 mm. Most preferably the thickness of the filter paper is about 0.175 mm. When a filter paper is used that has a thickness in excess of about 0.175 mm, it is possible that the area in which developing solution travels may correspondingly decrease; the opposite is possible for a filter paper that has a thickness less than about 0.175 mm. In order to compensate for these variables, at least two approaches are possible: (1) altering the amount of developing solution added to the filter paper; or (2) adjusting the location of the outer edges of the apertures relative to the target area. Thus, for a filter paper having a thickness greater than about 0.175 mm, more than two to three drops of developing solution can be utilized (about three to four drops), or the aperture, and hence, the outer edges of the aperture, can be moved closer to the target area. The opposite is suggested for filter paper having a thickness less than about 0.175 mm. I.e., less than about two drops of developing solution can be utilized (about one drop) or the aperture, and hence the outer edge of the aperture, can be moved further from the target area.

The particle size retention of the filter paper is defined herein as the average size of a spherical particle retained by a given filter paper with a 98% efficiency as determined using an electronic particle counter. Preferably, this value is relatively small, on the order of from less than about 1.0 micron to about 7.0 microns. Most preferably, the particle size retention is about 4.0 microns. The value for the particle size retention cannot be such a value that too much of the sample is able to "leak" through the filter paper, while at the same time if the value is too small, the sample will not properly diffuse through the filter paper. Adjustment of the distance of the outer edge of the aperture relative to the particle size retention is made in the same manner as that of the thickness of the filter paper. Accordingly, as the particle size retention value increases, the outer edge distance from the target area increases, and as the particle size retention value decreases, the outer edge distance from the target area decreases.

Related to particle size retention is the flow rate or linear wicking of the filter paper. This value can be defined in a variety of ways depending on the manufacturer of the filter paper. Preferably, the flow rate (which can be defined in terms of the time necessary for distilled water to rise a specified distance on the filter paper) is between about 0.3 cm/minute and about 0.9 cm/minute. Most preferably, the flow rate is about 0.6 cm/minute. The flow rate value is of import in that diffusion of the sample is related to the flow rate of the filter paper. Thus, as flow rate increases, the outer edge distance from the target area increases, and as the flow rate decreases, the outer edge distance from the target area decreases.

ADVANTAGES OF THE INVENTION

The advantages derived from the present invention include the placement of a consistent quantity of sample applied in a consistent manner to a consistent location on test sheet 101 such that addition of a developing solution close to but not directly into the diffusion area allows the developer to migrate through the diffusion area, carrying the resultant color (e.g. blue when guaiac treated paper is utilized) away from the dark background of the diffused region, thus increasing and enhancing the readability of the reaction. These advantages are derived from locating the aperture relative to the indicating means. Furthermore, because the patient is instructed to completely fill the aperture, variations in the amount of sample added to a specimen slide are avoided as well as the aforementioned concerns associated with such variations. Additionally, because specimen slide 100 does not yield any additional sub-parts or components which may require separate disposal, the entire slide can be disposed upon completion of development, thereby reducing the potential for improper disposal of a clinical material.

While the present invention has been set forth in considerable detail, the invention disclosed herein is not to be limited to the detailed description, but is to be afforded the full scope of the appended claims and all equivalents thereto.

What is claimed is:

1. A specimen slide comprising:
   (a) a front panel including an aperture said aperture having a width, a height, an outer edge and an inner edge;
   (b) a back panel including a flap means opposite to said aperture;
   (c) a sheet carried between said front and said back panel and positioned for receiving a specimen through said aperture;
   (d) a cover adapted to overlie and close said aperture; and
   (e) means for directing placement of a solution onto an area of said sheet on a back panel side of said slide opposite to that of said aperture, said directing means being located on said sheet between about 1.5 and about 2.5 times the width of said aperture from the outer edge thereof.

2. The specimen slide of claim 1 wherein the width of said aperture is between about 0.25 cm and about 1.00 cm.

3. The specimen slide of claim 2 wherein the height of said aperture is about 4.0 times the width.

4. The specimen slide of claim 1 wherein said width is about 0.50 cm.

5. The specimen slide of claim 1 wherein the height of said aperture is between about 5.0 times and about 1.5 times the width.

6. The specimen slide of claim 1 wherein said aperture has a letter C configuration.

7. A specimen slide comprising:
   (a) a front panel including an aperture said aperture having a width, a height, an outer edge and an inner edge;
   (b) a back panel including a flap means opposite to said aperture;
   (c) a sheet carried between said front and said back panel and positioned for receiving a specimen through said aperture;
   (d) a cover adapted to overlie and close said aperture; and
   (e) means for directing placement of a solution onto an area of said sheet on a back panel side of said slide opposite to that of said aperture, said directing means being located on said sheet about 2.00 times the width of said aperture from the outer edge thereof.

8. The specimen slide of claim 7 wherein said width is about 0.50 cm.

9. A specimen slide comprising:
   (a) a front panel including at least two apertures said apertures having a width, a height, an outer edge and an inner edge where the inner edges of each aperture are substantially non-parallel with each other;
   (b) a back panel including flap means opposite to said apertures;

(c) a sheet carried between said front panel and said back panel and positioned for receiving a specimen through said apertures;

(d) a cover adapted to overlie and close said apertures; and wherein the distance between the outer edge of a first aperture and the outer edge of another aperture is between about 3.0 times and about 5.0 times the width of said first aperture.

10. The specimen slide of claim 9 further comprising means for directing placement of solution onto the sheet on the back panel side of the slide, said means being located on said sheet opposite to said apertures at an approximate midpoint between the first aperture and the other aperture.

11. The specimen slide of claim 9 wherein the width of said aperture is between about 0.25 cm and about 1.00 cm.

12. The specimen slide of claim 9 wherein the width of said apertures is about 0.50 cm.

13. A specimen slide comprising:

(a) a front panel including at least two apertures said apertures having a width, a height, an outer edge and an inner edge where the inner edges of the apertures are substantially non-parallel with each other;

(b) a back panel including flap means opposite to said apertures;

(c) a sheet carried between said front panel and said back panel and positioned for receiving a specimen through said apertures;

(d) a cover adapted to overlie and close said apertures; and wherein the distance between the outer edge of a first aperture and the outer edge of another aperture is about 4.0 times the width of said first aperture.

14. The specimen slide of claim 13 further comprising means for directing placement of solution onto the sheet on the back panel side of the slide, said means being located on said sheet opposite to said apertures at an approximate midpoint between the first aperture and the other aperture.

15. The specimen slide of claim 13 wherein the width of said apertures is between about 0.25 cm and about 1.00 cm.

16. The specimen slide of claim 13 wherein the width of said apertures is about 0.50 cm.

17. A specimen slide comprising:

(a) a front panel including an aperture having a width and an outer edge;

(b) a sheet carried by said front panel and positioned for receiving a specimen through said aperture; and (c) means for directing placement of a solution onto an area of said sheet on a back panel side of said slide opposite to that of said aperture, said directing means being located on said sheet between about 1.5 and about 2.5 times the width of said aperture from the outer edge thereof.

18. The specimen slide of claim 17 wherein the width of said aperture is between about 0.25 cm and about 1.00 cm.

19. The specimen slide of claim 17 wherein said width is about 0.50 cm.

20. The specimen slide of claim 17 wherein the height of said aperture is between about 5.0 times and about 1.5 times the width.

21. The specimen slide of claim 17 wherein said aperture has a letter C configuration.

22. A specimen slide comprising:

(a) a specimen receiving sheet;

(b) an aperture abutting a sample receiving side of the sheet said aperture having a defined width and an outer edge; and (c) means for directing placement of a solution within proximity to an area on said sheet, said area being located between about 1.5 and about 2.5 times the width of said aperture from the outer edge of said aperture.

23. A specimen slide comprising:

(a) a front panel including two apertures, said apertures having substantially the same letter C configuration, each aperture defined by a width, a height, an outer edge and an inner edge;

(b) a back panel including a flap means opposite to said apertures;

(c) a sheet carried between said front and said back panel and positioned for receiving a specimen through said apertures;

(d) a cover adapted to overlie and close said apertures; and (e) means for directing placement of a solution onto an area of said sheet on a back panel side of said slide opposite to that of said apertures, said directing means being located on said sheet about 2.0 times the width of said apertures from the outer edges thereof, wherein the width of each aperture is about 0.50 cm.

24. A method for developing a specimen slide comprising a specimen receiving sheet and an aperture abutting a sample-receiving side of the sheet, said aperture having a defined width and an outer edge, the method comprising the.. step of placing a developing solution onto an area of said sheet opposite to the sample-receiving side of the sheet, said area being located between about 1.5 and about 2.5 times the width of said aperture from the outer edge of said aperture.

* * * * *